United States Patent [19]

Gross

[11] Patent Number: 5,407,434
[45] Date of Patent: Apr. 18, 1995

[54] AUTOMATIC LUMEN VISCOUS RESEAL

[75] Inventor: James R. Gross, Wareham, Mass.

[73] Assignee: The Kendall Company, Mansfield, Mass.

[21] Appl. No.: 186,943

[22] Filed: Jan. 27, 1994

[51] Int. Cl.6 ...................... A61M 5/178; A61M 5/00; F15B 21/00
[52] U.S. Cl. ..................................... 604/167; 604/245; 604/256; 137/807
[58] Field of Search ........................ 137/251, 247, 807; 604/122-125, 164, 167, 169, 245-247, 256, 283, 30, 37

[56] References Cited

U.S. PATENT DOCUMENTS

| | | | |
|---|---|---|---|
| 3,035,600 | 5/1962 | Gilmont | 137/247 |
| 4,460,018 | 7/1984 | Sweeney | 137/807 |
| 4,540,411 | 9/1985 | Bodicky | 604/169 |
| 4,932,938 | 6/1990 | Goldberg et al. | 604/96 |
| 5,071,411 | 12/1991 | Hillstead | 604/246 |
| 5,078,689 | 1/1992 | Keller | 604/167 |
| 5,088,980 | 2/1992 | Leighton | 600/30 |
| 5,108,375 | 4/1992 | Harrison et al. | 604/167 |
| 5,122,121 | 6/1992 | Sos et al. | 604/167 |

Primary Examiner—John D. Yasko
Assistant Examiner—Adam J. Cermak
Attorney, Agent, or Firm—Alvin Isaacs

[57] ABSTRACT

The invention features a needle defining a flowpath, a housing comprising a proximal end and a distal inner seat leading to and defining a lumen, and a viscous material contained within the housing. The needle is slidable through the housing and the viscous material contained therein. The viscous material is fluid enough for the needle to slide therethrough, yet semi-solid enough to conform to the housing distal inner seat so as to form a seal thereat and prevent flow of fluid or air through the lumen.

13 Claims, 3 Drawing Sheets

5,407,434

AUTOMATIC LUMEN VISCOUS RESEAL

FIELD OF THE INVENTION

The invention relates in general to a thoracentesis device which is used in the removal of fluid from the pleural cavity, and specifically to a thoracentesis device which prevents air entry into the pleural cavity and lung puncture during use.

BACKGROUND OF THE INVENTION

It is an object of the invention to perform the medical procedure know as thoracentesis, i.e., removal of air, blood, intrathoracic fluid, or other secretions from the pleural cavity, without allowing air to be pulled from outside of the body into the pleural cavity.

SUMMARY OF THE INVENTION

The invention features a needle containing a flowpath for flow of air or fluid, a housing comprising a proximal end and a distal inner seat leading to and defining a lumen, wherein the needle is slidable through the housing, and a viscous material contained within the housing, the viscous material being fluid enough for the needle to slide therethrough, yet semi-solid enough to conform to the housing distal inner seat so as to form a seal thereat and prevent flow of fluid or air through the lumen.

In preferred embodiments of the invention, the material may be any material which possesses enough self-adherence to form a seal, yet lacks dimensional stability; for example, silicone, e.g, a heavy semi-cross-linked silicone gel, or a semi-solid viscous material such as a lubricating gel. When the needle is withdrawn from the housing, the viscous material contracts to fill up space left by removal of the needle.

In other preferred embodiments, the housing is attached to a catheter tube defining a lumen that is contiguous with the lumen to which the housing distal inner seat leads. Thus, the catheter tube lumen is in fluid or air communication with the housing inner seat and is sealed off from the external environment when the needle is removed from the housing and the viscous material forms a seal against the housing distal inner seat.

The catheter tube may include a soft tip. The housing may be connected to the catheter tube via a bifurcated hub comprising two converging conduits, one conduit being in communication with the housing.

In yet other embodiments, a syringe, defining a chamber, is attached to the needle proximal end such that the syringe chamber is in fluid or air communication with the needle flowpath. A plunger is slidable within the syringe chamber. The plunger may include a compressed spring wound around the plunger and biased against the plunger and the syringe so as to urge the plunger out of the syringe chamber and thus create a negative atmospheric pressure in the syringe chamber, and thus also inside the needle. The syringe chamber may include a preservative, e.g., an anti-coagulant, for preservation of plural effusion drawn into the syringe during use.

The invention also includes methods of performing thoracentesis, comprising inserting a lumen reseal device described herein into the body of a patient until the needle encounters the pleural cavity, the needle defining a flowpath containing air, wherein a change in pressure through the needle flowpath indicates encounter of the needle with the pleural cavity.

Preferably, the method also includes the step of removing the needle from the patient after encounter with the pleural cavity, wherein upon removal of the needle from the housing promotes formation of a viscous seal against the housing inner seat so as to prevent the entrance of air into the pleural cavity.

Other features and objects will become apparent from the description of the invention and from the claims.

DESCRIPTION OF THE PREFERRED EMBODIMENT

Thoracentesis involves the insertion of a tube or catheter through an incision in the chest wall into the pleural cavity. After insertion of the catheter and removal of the needle, the leading end of the catheter is connected to a negative pressure source, e.g., a pump, and fluid is then removed from the pleural cavity through the catheter. In order for the lungs to remain expanded during this procedure, it is important to insure that the needle does not puncture the lungs. It is also highly desirable to keep the pleural cavity sealed at all times from the atmosphere. Thus, removal of fluid from the pleural cavity presents problems unique to this body cavity.

Figure 1:
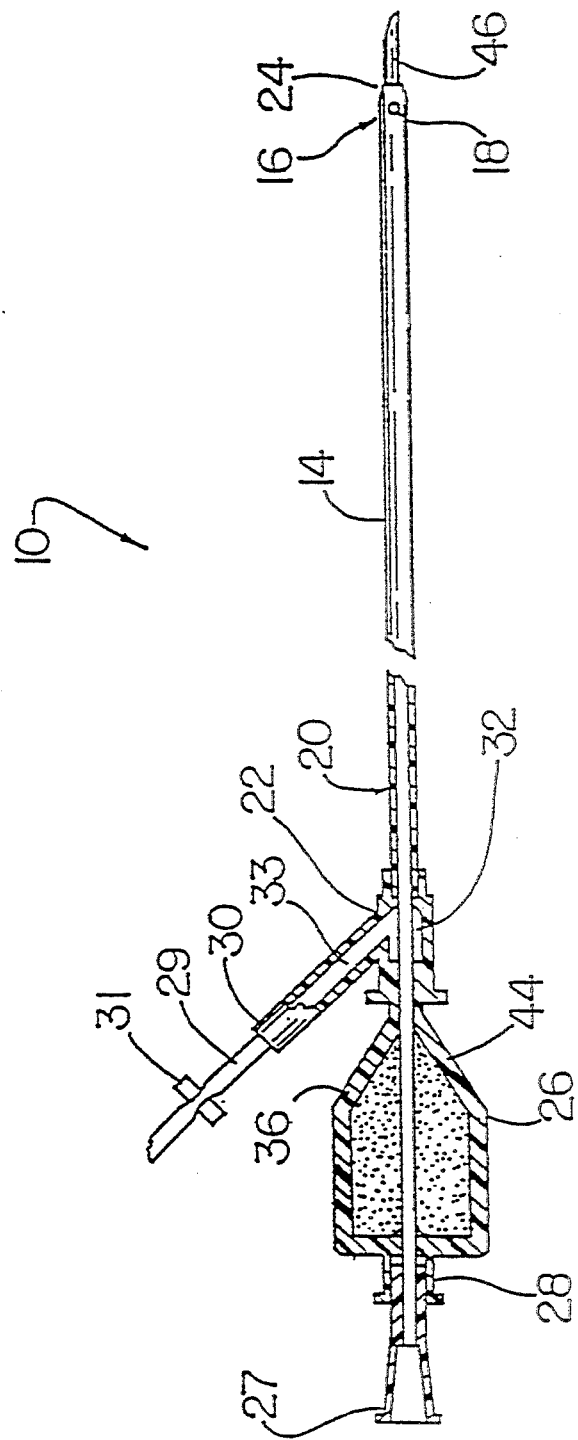
FIG. 1 is a cross-sectional view of an automatic needle lumen reseal device of the invention joined to a catheter tube and side-arm.

A thoracentesis device of the invention 10 is shown generally in FIG. 1. The device 10 includes an elongated flexible catheter 14 having a leading end 16 formed with one or more radial ports or openings 18 which allow for fluid or air communication with the body cavity to which the leading end is inserted. The catheter leading end 16 may be tapered as shown 24. The catheter 14 has a trailing end 20 connected to an bifurcated conduit 22 defining a lumen 32 that is in line with the catheter 14 and a lumen 33 that is in line with side-arm 30. Device 10 includes a hollow barrel or housing 26 and adapter 28 which connects to barrel 26. Adapter 28 and barrel 26 are aligned such that they define a space which leads to lumen 32.

For ease of description, the ends of the components of the device described herein are referred to as leading and trailing; i.e., the leading end referring to the end which encounters the body first upon insertion or which is closer to the body during use. The ends of the housing itself are referred to as proximal, i.e., the end closest to the user of the device, and distal.

Figure 2:
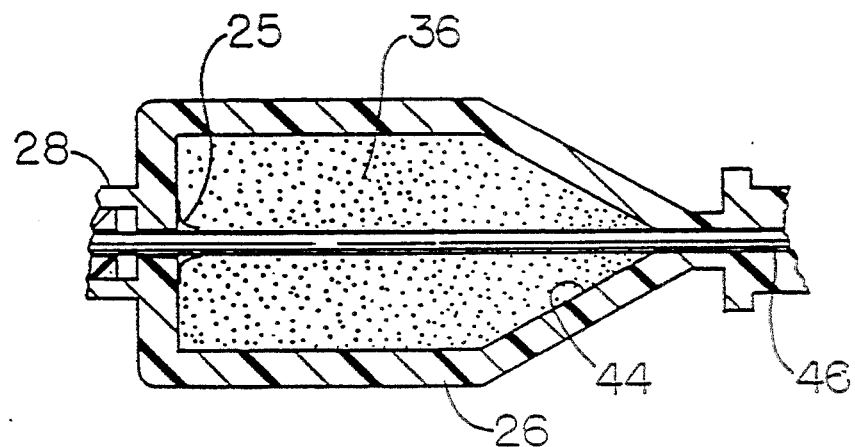
FIG. 2 is an enlarged cross-sectional view of one embodiment of the automatic lumen reseal device of FIG. 1 in which the needle is inserted.
Figure 3:
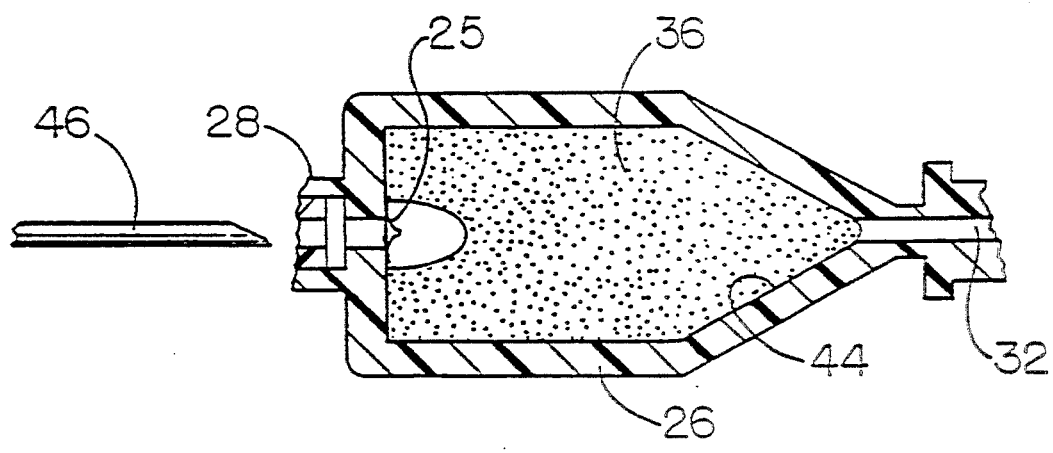
FIG. 3 is an enlarged cross-sectional view of one embodiment of the automatic lumen reseal device of FIG. 1, corresponding to FIG. 2, in which the needle is removed.

Referring to FIGS. 2 and 3, in accordance with the present invention, barrel 26 includes an automatic seal which serves to reseal air or fluid flow through catheter 14 to or from outside the body. Thus, the automatic seal includes a viscous sealing material 36 which, upon removal of the needle 46 from the housing 26, forms a seal against the inner seat 44 of housing 26 to seal lumen 32 from the atmosphere.

A hollow needle 46 having a sharpened leading end extends through lumen 32, conduit 22 and catheter 14, and beyond the leading end 16 of catheter 14 if desired.

In accordance with the invention, the automatic seal is self-sealing, and is operable to seal the lumen 32 upon withdrawal of the needle from catheter 14 and housing 26. Thus, withdrawal of the needle 46 from the catheter 14 is effected by pulling the needle 46 back and out of lumen 32. Sealing material 36 then forms a seal against inner seat 44 of barrel 26 when needle 46 is withdrawn. The sealing material 36 is a viscous material which is fluid enough to allow unimpeded movement of the needle 46 therethrough, but semi-solid enough to self-adhere and fit sealingly into the inner seat 44 of barrel 26 and thus to close the lumen 32 to the outside air. Viscous material 36 is not fluid enough to flow through catheter tube 14. The automatic seal is designed so that re-insertion of the needle after it has been fully withdrawn is prevented. Thus, if after removal of needle 46 from housing 26, re-insertion of needle 46 is attempted, the needle tip would become contaminated with viscous sealing material. In addition, re-insertion of needle 46 through housing 26 and into catheter 14 would push the viscous sealing material through the catheter tube 14 alongside the needle 46, thus potentially introducing the sealing material into the patient.

FIG. 2 is a schematic and enlarged representation of one embodiment of an automatic seal of the invention. In this embodiment of the invention, as in other embodiments, the inner seat 44 of the barrel 26 provides a shape to which the sealing material 36 may easily and sealingly conform upon removal of needle 46 from barrel 26. The sealing material is too viscous to exit housing 26 via adapter 28. Housing 26 may include a flexible sealing flap 25 through which the needle pushes during insertion into or removal from barrel 26, the sealing flap thus preventing exit of material 36 from barrel 26. In the unsealed position depicted in FIG. 2, the needle 46 passes through sealing material 36 and is aligned with lumen 32. As shown in enlargement in FIG. 3, upon removal of needle 46 from barrel 26, the sealing material 36 contracts so as to occupy a smaller space, i.e., the space which the needle occupies when inserted within barrel 26. In the sealed position depicted in FIG. 3, the sealing material 36 has assumed a position against inner seat 44 of barrel 26 which seals off lumen 32 from the outside air. Thus, upon sealing, neither air nor fluid can pass from the outside to lumen 32 in catheter 14.

In the automatic viscous seal of the invention, the seal formed by the sealing material against the inner seat 44 of barrel 26 is created by an extremely snug, i.e., a sealing, fit between the closely conforming characteristic of the sealing material and the inner seat 44 of barrel 26.

Needle 46 is sized so as to pass freely through the lumen 32 of conduit 22 and all the way through the catheter 14 so that the beveled leading end of needle 46 extends a short distance beyond the leading end 16 of catheter 14. At its leading end, the needle 46 is attached to a leur hub 27 which is engageable with adapter 28 to limit axial movement of the needle 46 relative to adapter 28.

The sealing material is made of any material which is fluid enough to allow easy passage of the needle therethrough, yet must also be capable of forming an effective and reliable seal around the needle at both ends of the housing. In addition, the material must be semi-solid enough to be incapable of flowing through the catheter tube 14, yet still lack dimensional stability. The viscous material may be, for example, a semi-solid gel, a semi-cross-linked gel, e.g., polyvinylpyrrolidone, silicone, mineral oil, viscosified liquids and the like, having a viscosity on the order of 50,000–100,000 cps. Such materials are well-known in the art and are obtainable from Dow Chemical Co.

Side-arm 30, which defines lumen 33 that also leads into lumen 32, is for removal or delivery of liquid through the catheter 14. Side-arm 30, leading to extension tube 29, will normally be maintained such that it is blocked, e.g., using a clamp 31 or similar means around extension tube 29. After insertion of catheter 14 into the body, side-arm 30 may be connected via a tube to a vacuum bottle or the like. Thus, in withdrawal of fluid, e.g., the vacuum bottle is used to collect fluid or other matter from the pleural cavity. In addition, the rate of fluid removal from the body may be controlled using the clamp, e.g., a roller clamp.

Catheter 14 will preferably include a soft or blunted tip. For example, the catheter tip may be insert-molded or injection-molded into a shape which blunts the tip enough to avoid piercing the lung, but not enough to prevent entry of the tip into the body cavity. For example, the shape of the tip may be altered to provide a blunt effect, e.g., by narrowing the tip in a cone shape, and then flaring the edge back. Alternatively, the narrowed, cone-shaped tip may be over-molded with a tip of a softer material than the shaft of the catheter. Thus, the softer-tipped catheter tip will be less likely to damage the lung during insertion of the catheter into the body. The integral soft tip is made as follows. A mold is provided which is capable of forming the catheter tip into the desired shape. The softer portion of the catheter tip may measure, e.g., about ⅛ of an inch. The leading end of the catheter tube, including an open end, is placed into the mold, and a pin is inserted into the open end of the catheter tip to preserve the lumen of the catheter during molding. A lower durometer molten plastic is injected into the mold around the catheter leading end, and the plastic is allowed to cool and harden. The newly-formed soft tip is then removed from the mold. Materials of different durometers may be used to form the soft integral catheter tip which is softer than the material from which the catheter tube itself is made. The catheter tube may be made of an elastomeric material such as polyurethane, and the tip made of a lower durometer polyurethane. For example, the catheter tube may be made of Tecoflex (Woburn, Mass.) medical grade aliphatic polyurethane 100A, and the tip of polyurethane 60A or 80A. The softer-tipped catheter tip will be less likely to damage the lung during insertion of the catheter into the body.

Figure 4:
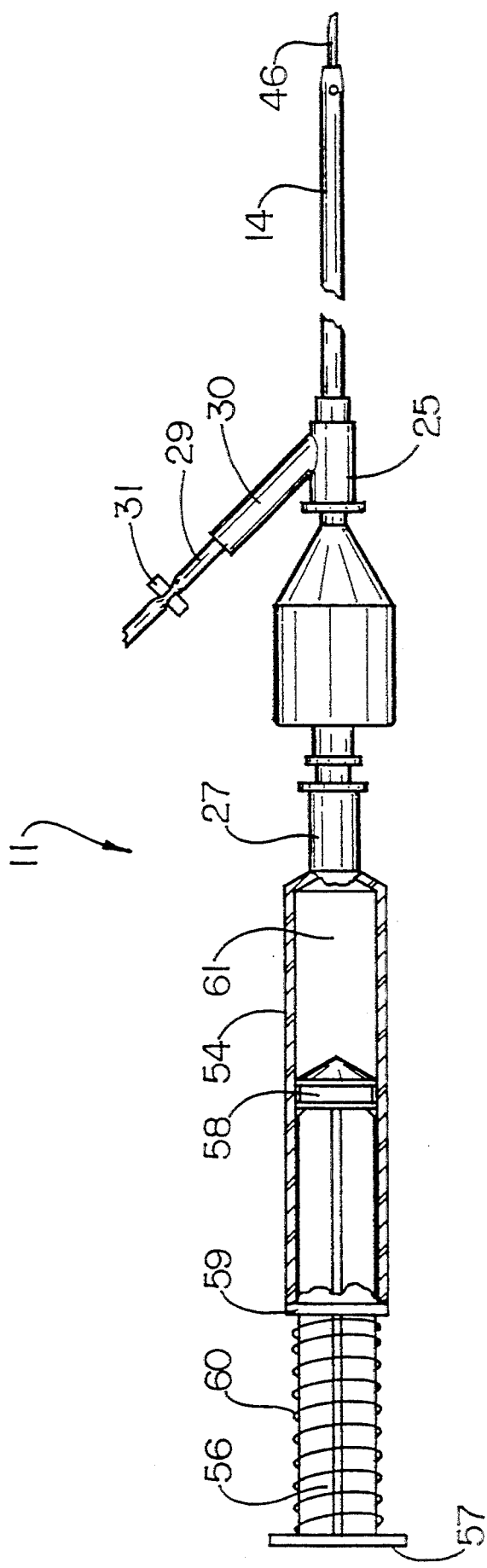
FIG. 4 is a catheter device in which the needle is connected with a plunger and syringe.

In a preferred embodiment of the invention shown in FIG. 4, the device 10 includes means for applying pressure within the flowpath defined by the needle, the means including a syringe/plunger combination. Thus, leur hub 27 joins the trailing end of needle 46 to a syringe 54 such that the flowpath defined by needle 46 is in fluid communication with syringe chamber. Leur hub 27 contains a hole to allow the flowpath defined by needle 46 to be in fluid communication with the syringe chamber 61. A plunger 56 is slidable within the syringe 54 and includes leading end 58 such that when the plunger 56 is withdrawn outwardly from the syringe 54, a negative pressure is created within the syringe chamber and is effected throughout the flowpath within needle 46. As shown in FIG. 4, outward movement of plunger 56 within syringe 54 may be effected by an optional compression spring 60 wound around the plunger and creating a bias against the plunger trailing end 57 and the syringe trailing end 59. The compression spring 60 is thus maintained under compression to create an automatic suction for location of the pleural space in the patient's body. Once the pleural space is located, intrathoracic fluid may be removed.

Referring to FIGS. 1-4, the devices 10 and 11 of the invention may be used in thoracentesis as follows. The beveled needle 46 is used to penetrate a chest wall or back of the patient and to locate the pleural cavity. The tapered end 24 of catheter 14 follows closely behind the beveled needle end 46 through the chest wall. As soon as the leading catheter end 16 is within the chest wall, negative pressure is applied within the flowpath defined by needle 46 by pulling rearwardly on plunger 56 or by allowing compression spring 60 to be released slightly such that the plunger 56 moves out of the syringe 54. Penetration of the patient's body by the needle 46 and catheter 14 is resumed. When the needle 46 passes through the chest wall or back and into the pleural cavity, negative pressure within the needle causes fluid in the pleural cavity to be drawn through the needle and into the syringe chamber. This will be visible immediately to the surgeon such that he or she knows the needle point has reached the pleural cavity. The device is inserted slightly further to insure that the catheter leading end 16 is in the pleural cavity, but not far enough for the needle to penetrate the lung.

The syringe 54 and plunger 56, and needle 46, are then removed from the catheter 14, leaving the catheter 14 in place in the pleural cavity. Upon removal of needle 46, the automatic lumen reseal device of the invention creates a seal within the housing by sealingly conforming to the inner seat of the housing, at the portion where the housing leads to the catheter lumen 32. The seal thus created prevents air from entering the pleural cavity. Thus, fluid or air communication between the pleural cavity of the patient and the outside atmosphere is completely avoided according to the invention. Once the needle is withdrawn, danger of lung puncture is substantially eliminated even if the leading catheter end 16 engages the lung since the catheter 14 is flexible and its leading tip 24 relatively soft or blunt, as described herein. Because the catheter 14 is relatively flexible in comparison to the needle 46, the danger of puncturing the lung is substantially eliminated after removal of the needle, particularly using a soft-tipped catheter 14. The catheter itself is sufficiently flexible so as to pose little threat of puncturing the lung.

Once the needle has been removed and the automatic lumen reseal is effected, the side-arm 30 may be connected to a vacuum source such as a vacuum bottle. The vacuum bottle may be used to withdraw fluid from the pleural cavity. The rate at which fluid is withdrawn from the pleural cavity is controlled by clamp 31. The tightness of the clamp on the extension tubing 29 is controlled manually.

It will be appreciated that the thoracentesis procedure described above is carried out without air or fluid communication between the pleural cavity in the patient's body and the external environment. Thus, no air is allowed to enter the pleural cavity, and the threat of lung puncture and collapse is avoided. Once the leading end 16 of the catheter 14 is positioned within the pleural cavity, the lumen 32 is sealed from the atmosphere both when the needle 46 is inserted within the catheter 14 by virtue of the syringe and automatically upon removal of the needle 46 from the catheter 14 and housing 26.

OTHER EMBODIMENTS

Although the invention has been described with reference to the preferred embodiment illustrated in the drawings, other modifications of the invention will be apparent to those skilled in the art without departing from the spirit or scope of the invention.

It is claimed:

1. A lumen reseal device, comprising
a needle defining a flowpath,
a housing comprising a proximal end and a distal end, the distal end having an inner seat leading to and defining an open lumen distal to said inner seat, wherein the needle is slidable through the housing,
a viscous material contained within the housing, the viscous material being fluid enough for the needle to slide therethrough, yet semi-solid enough to conform to the housing distal inner seat, without flowing into said lumen, so as to form a seal thereat upon removal of the needle from the housing.

2. The lumen reseal device of claim 1 wherein the viscous material is a semi-solid material.

3. The lumen reseal device of claim 2, said viscous material comprising a semi-cross-linked gel.

4. The lumen reseal device of claim 2, said semi-solid material comprising a lubricating gel.

5. The lumen reseal device of claim 1 wherein the material is selected from the group consisting of: silicone, mineral oil, polyvinylpyrollidone, and a viscosified liquid having a viscosity on the order of 50,000–100,000 cps.

6. The lumen reseal device of claim 1 further including a catheter tube attached to the housing and defining a lumen that is contiguous with the lumen to which said housing distal inner seat leads, the catheter tube lumen being in fluid communication with the housing inner seat and being sealed off from the external environment when the needle is removed from the housing and the viscous material forms a seal against the housing inner seat.

7. The lumen reseal device of claim 6 further including a bifurcated hub comprising two converging conduits, said bifurcated hub connecting said housing to said catheter tube, one said conduit being in communication with said housing.

8. The lumen reseal device of claim 6, said catheter tube comprising a soft tip.

9. The lumen reseal device of claim 8, said soft tip being integral with said catheter.

10. A lumen reseal device, comprising
a needle defining a flowpath,
a housing comprising a proximal end and a distal inner seat leading to and defining a lumen, wherein the needle is slidable through the housing,
a viscous material contained within the housing, the viscous material being fluid enough for the needle to slide therethrough, yet semi-solid enough to conform to the housing distal inner seat, without flowing into said lumen, so as to form a seal thereat;
a syringe having leading and trailing ends and defining a chamber,
a plunger having leading and trailing ends, said plunger leading end being movable within said syringe chamber, a compressed spring wound around said plunger and biased against said plunger trailing end and said syringe trailing end so as to urge said plunger out of said syringe chamber, wherein said syringe is connected to said housing distal end such that said syringe chamber is in fluid communication with said needle flowpath.

11. The lumen reseal device of claim 10 wherein the syringe chamber contains an anti-coagulant.

12. A device for thoracentesis, comprising
a needle defining a flowpath,
a housing comprising a proximal end and a distal inner seat leading to and defining a lumen, wherein the needle is slidable through the housing,
a viscous material contained within the housing, the viscous material being fluid enough for the needle to slide therethrough, yet semi-solid enough to conform to the housing distal inner seat, without flowing into said lumen, so as to form a seal thereat upon removal of the needle from the housing;
a catheter tube attached to the distal end of the housing and defining a lumen that is contiguous with the lumen to which said housing distal inner seat leads, the catheter tube lumen being in fluid communication with the housing inner seat and being sealed off from the external environment when the needle is removed from the housing and the viscous material forms a seal against the housing inner seat.

13. The lumen device of claim 12, further comprising
a syringe having leading and trailing ends and defining a chamber,
a plunger having leading and trailing ends, said plunger leading end being movable within said syringe chamber,
a spring biased to urge said plunger out of said syringe chamber, wherein said syringe is connected to said housing distal end such that said syringe chamber is in fluid communication with said needle flowpath.

* * * * *